United States Patent
Pillion

[11] Patent Number: 5,844,125
[45] Date of Patent: Dec. 1, 1998

[54] METHOD AND APPARATUS FOR MEASURING MOISTURE CONTENT IN A GAS

[75] Inventor: John E. Pillion, Brookline, N.H.

[73] Assignee: Millipore Corporation, Bedford, Mass.

[21] Appl. No.: 941,977

[22] Filed: Oct. 1, 1997

[51] Int. Cl.⁶ .............. G01W 1/00; G25F 3/20; G01N 31/00; H01C 13/00

[52] U.S. Cl. .......... 73/29.01; 73/335.04; 73/31.02; 73/579; 422/83

[58] Field of Search .............. 73/29.01, 31.02, 73/335.04, 31.06, 31.03; 422/83

[56] References Cited

U.S. PATENT DOCUMENTS

| | | | |
|---|---|---|---|
| 3,523,244 | 8/1970 | Goodman et al. | 324/61 |
| 3,642,521 | 2/1972 | Moltzan et al. | 117/105.2 |
| 4,143,177 | 3/1979 | Kovac et al. | 427/79 |
| 4,163,384 | 8/1979 | Blakemore | 73/29 |
| 4,164,868 | 8/1979 | Suntola | 73/336.5 |
| 4,765,870 | 8/1988 | Emmer et al. | 204/129.1 |
| 4,793,182 | 12/1988 | Djorup | 73/336.5 |
| 5,198,094 | 3/1993 | Mettes | 204/430 |
| 5,199,295 | 4/1993 | Mettes | 73/1 G |
| 5,317,274 | 5/1994 | Nakagawa et al. | 324/678 |
| 5,319,975 | 6/1994 | Pederson et al. | 73/335.01 |
| 5,591,896 | 1/1997 | Lin | 73/31.05 |
| 5,616,827 | 4/1997 | Simmermon et al. | 73/29.01 |

FOREIGN PATENT DOCUMENTS

| | | |
|---|---|---|
| 278171 | 9/1993 | Czechoslovakia . |
| 03269356 | 11/1991 | Japan . |
| 05149897 | 6/1993 | Japan . |
| 08026790 | 1/1996 | Japan . |
| 1332225 | 8/1987 | U.S.S.R. . |

*Primary Examiner*—Hezron Williams
*Assistant Examiner*—J. David Wiggins
*Attorney, Agent, or Firm*—John Dana Hubbard; Timothy J. King; Paul J. Cook

[57] ABSTRACT

A device for measuring moisture concentration in a gas is provided which includes a sensing device capable of producing physical response to an energy input and having at least one surface coated with a metal hydroxide capable of adsorbing moisture. The metal hydroxide is derived from a metal coating on the sensing device.

18 Claims, 5 Drawing Sheets

METHOD AND APPARATUS FOR MEASURING MOISTURE CONTENT IN A GAS

BACKGROUND OF THE INVENTION

1. Field of the Invention

The invention relates to a method and apparatus for detecting water impurity in a gas stream. More particularly, this invention relates to a method for detecting water impurity with a sensing device coated with a metal hydroxide derived from a metal and which adsorbs water.

2. Description of the Prior Art

At the present time, ultrapure gas streams are utilized in chemical reactions such as in the pharmaceutical and semiconductor industry. These chemical reactions usually are conducted in sealed containers to maintain purity since the gases often times are toxic and are conducted under low pressure in order to decrease the probability of unwanted side reactions. In order to maintain the requisite gas purity, the gas is treated, prior to entering the reaction chamber, in order to remove impurities therefrom. It is general practice to pass the gas through a bed of resin particles which are interactive with impurities such as water in the gas. Over time, the capacity of the bed of resin particles for interacting with the impurities is depleted to a point where breakthrough of impurities from the resin bed occurs and the impurities enter the reaction zone. It is difficult to predict when undesirable depletion of resin capacity occurs so that, in the absence of independent monitoring means, premature or late removal of the resin is likely. Premature resin removal results in expensive damage to reaction product. It is additionally desirable to have a means for continuously monitoring the gas purity level and providing a measure of gas impurity concentration.

It is also desirable to provide a moisture sensor which renders it useful for in-line moisture detection applications, particularly near the point of end use of the gas. Presently available moisture monitors require auxiliary apparatus such as heaters, moisture sources or gas purifiers which effectively increase their size, causing them to become inconvenient for placement near the point of end use of the gas.

At the present time, a variety of sensing devices are utilized to measure moisture content in a gas. These sensing devices include chilled mirror hygrometers, spectrophotometric, piezoelectric including surface acoustical wave (SAW) devices, colormetric, electrolytic and capacitive devices. These devices are coated with a composition which interacts with moisture such as by being reacted therewith, adsorption or chemisorption. As a result of contact with moisture in a gas stream, at least one characteristic of the coating changes, such as a change in mass, conduction, capacitance or the like. This change can be correlated to moisture concentration in the gas by comparing the change in coating characteristic with a previously generated standard relationship between the coating characteristic measured and moisture concentration in the gas.

It has been proposed in U.S. Pat. No. 4,765,870 to provide a coating for a moisture sensing device comprising aluminumoxihydroxide which is formed by hydration of a sputtered aluminum film with boiling water. Undesirable extended reaction times and heating with boiling water are required to form the oxihydroxide of sufficient thickness suitable for sensing moisture.

It has also been proposed to utilize powdered metal hydroxide formed from powdered metal oxides as a moisture sensor by Japanese Patent Nos. 08026790 and 05149897. The coating method requires transfer of the metal to a sensing container which is inconvenient. In addition, a powder is a source of particles which are incompatible with cleanroom manufacturing techniques such as are used to manufacture silicon wafers.

Soviet Union Patent 1,332,225 discloses the use of zeolites impregnated with potassium hydroxide and glycerol and heated to 200° C. to be used as moisture sensors. The presence of organic materials, such as glycol, in the sensor is not tolerable in semiconducting manufacturing environment. Potassium ions are incompatible with semiconductor wafer manufacturing process because they lead to mobile charges in $SiO_2$ gate oxide structures, which alter semiconductor device performance. Impregnating zeolites with metal hydroxides to obtain reproducible sensors is difficult because of differences in zeolite particles size and length of time required to obtain uniform impregnation throughout the solid.

Japanese Patent 03269356 discloses the use of a porous ceramic support impregnated with sodium hydroxide as a moisture sensor. Sodium ions are incompatible with semiconductor wafer manufacturing processes and are also deleterious to ion implantation.

Reversible moisture sensors are those which are not consumed during the moisture sensing process and which can be returned to an initial state which corresponds to an approximately zero moisture condition in the gas. Present reversible sensors include a relatively thick polymeric coating used in present moisture monitors. The thick coating requires that moisture only be allowed to contact the sensor for a small period of time. Thereafter, a span gas is applied to the sensor which is a gas that contains a known amount of moisture against which the sensor response is referenced. The span gas and sampled gas are switched using pneumatic valves and hardware to control the valves U.S. Pat. Nos. 5,616,827 and 5,199,295. During the use of these monitors, moisture is added to the gas stream using a diffusion or permeation tube. The permeation or diffusion tube is used to calibrate the sensor and to protect the sensor and housing from extended dry gas use. Addition of moisture is undesirable when a gas free of moisture is required by the end user for an in-line application.

Accordingly, it would be desirable to provide a moisture sensor which is not a source of gas contamination such as from particles, ions or organics. Furthermore, it would be desirable to provide such a moisture sensor which can be manufactured without the need for a high surface area support for the moisture sensitive coating of the sensor. In addition, it would be desirable to provide such a sensor which is reversible in that it is capable of being utilized for extended periods in moist gas without being consumed and that it can also be used in dry gas for extended periods without the need for auxiliary equipment.

SUMMARY OF THE INVENTION

The present invention provides a moisture sensor which includes a sensing device coated on at least one surface with a metal hydroxide coating. The metal hydroxide coating is produced in situ on the sensing device by first depositing a metal composition coating comprising a metal or metal alloy on the sensing device. The deposited metal composition is capable of being converted to a metal hydroxide by reaction with moisture. The mass of the resultant metal hydroxide composition coating is sufficiently large so that the hydroxide can continue to adsorb moisture for the service lifetime that is desired, while not being so large as to undesirably interfere with the function of the sensing device.

DESCRIPTION OF THE SPECIFIC EMBODIMENTS

Figure 1:
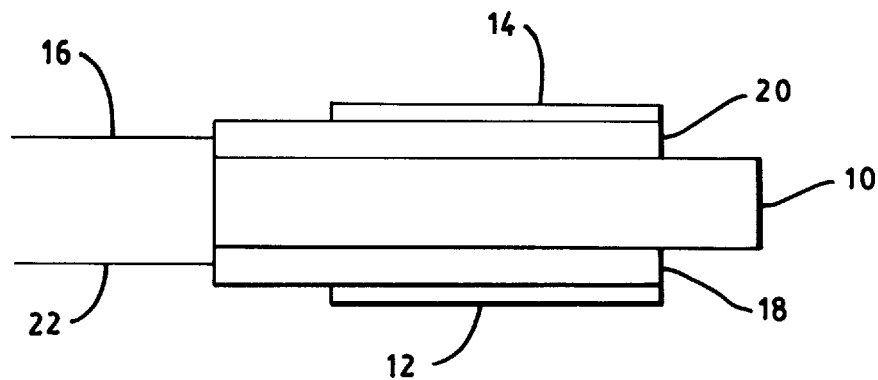
FIG. 1 is a side view of a coated piezoelectric sensing device of the invention.

This invention will be described in detail below with reference to a coated piezoelectric crystal as the sensing device for monitoring the presence of moisture. However, it is to be understood that the piezoelectric crystal can be replaced with alternative sensing devices which, when coated in accordance with this invention, can be utilized to measure moisture concentration in a gas. Such other sensing devices include colormetric devices, capacitive devices, conductivity devices, fiber optic devices or mass balances. The metal hydroxide coating of this invention interacts with the sensing devices so that the coating sensing device becomes capable of measuring moisture concentration in a gas. The metal hydroxide coating adsorbs moisture from the gas so that the effective means of sensing device is changed. This change, in turn, causes a change in the physical characteristics measured by the sensing device such as mass, conductivity, transmission, oscillation frequency, or dielectric constant. Energy is input to the sensing device and an energy output is measured. The measured physical characteristic then is compared to a previously generated standard relationship which correlates a measured physical characteristic with moisture concentration in a gas.

A capacitor having the metal hydroxide composition coating positioned between two plates and the capacitance, as a function of absorbed moisture of the composition, is measured is an example or a sensing device of this invention. The capacitance is measured accordingly in Equation 1:

$$\text{wherein: } C = \frac{C_{med} A}{4 \pi \kappa C_{vac} d}$$

C=measured capacitance
$C_{med}$=capacitance of the sensing medium
$C_{vac}$=capacitance of vacuum
A=the area of dielectric sensing material (cm$^2$)
k=electrostatic constant 8.99×10$^9$N m$^2$/C$^2$
d=thickness of dielectric sensing material Adsorption of moisture into the thin metal hydroxide composition coating will increase the capacitance of the composition and give an overall increase in the capacitance of the sensor. The change in capacitance is proportional to the moisture concentration in the gas contacting the sensor.

The coated piezoelectric crystals of this invention comprise a piezoelectric substrate such as natural quartz, lithium niobate, lead metaniobate, lead zirconate titanate, poly (vinylidene difluoride) (PVDF), Rochelle salts, tourmaline, ethylenediamine tartrate, dipotassium tartrate, ammonium dihydrogen phosphate, barium nitrite or the like, preferably quartz. The coating is applied to one or both of the largest surfaces of the substrate. The thickness shear mode behavior of piezoelectric materials can be explained using the Sauerbrey equation:

$$\Delta f = \frac{-n f_0^2 \Delta m}{A \sqrt{\rho_q \mu_q}}$$

wherein $\Delta f$ is the observed frequency charge, $f_o$, is the fundamental frequency of the crystal in Hz, $\Delta m$ is the mass change at the sensing surface in grams, n=1,2 is the number of sides of the crystal which are coated with the sensing medium, A is the piezoelectric active surface area of the deposit in cm$^2$, $\rho$ is the density of the piezoelectric crystal in grams/cm$^3$, and $\mu$ is the shear modulus of the piezoelectric crystal in grams/(sec$^2$cm$^2$). As evidenced by the equation, the observed frequency change is linearly dependent on the mass change but varies to the square of the fundamental frequency. Thus, a 2.0-MHz crystal will be four times more sensitive than a 1.0 MHz crystal.

The coating on the sensing device of this invention is formed by first depositing a metal or metal alloy on one or more surfaces of the sensing device. Suitable metals or metal alloys are those that react with water, to form a metal hydroxide composition, that the metal hydroxide composition thus formed permits detection of water at a concentration as low as 1 part per billion (ppb) and that the metal or the metal hydroxide composition does not add contaminant to a gas in contact with the metal or metal hydroxide composition. The metal or metal alloy can be deposited on a surface of the sensing device by any conventional means such as sputtering, vapor deposition, electroless deposition, electrolytic deposition or the like. The metal hydroxide composition derived from the metal or metal alloy does riot chemically react with water, but it physisorbs water. The metal or metal alloy should be reactive with water vapor at a partial pressure of 1×10$^{-6}$ torr and 2000 torr, preferably 1×10$^{-6}$ and 1×10$^{-1}$ torr, and at a temperature between about –100° C. and about 200° C. preferably between about 0° C. and about 35° C. to form the metal hydroxide composition under conditions which do not adversely affect the sensing device. Representative suitable metals include the Group 1A and IIA elements such as lithium, sodium, potassium, calcium, barium, mixtures thereof or as alloys with other metals such as iron, nickel, aluminum, gold copper, silver or alloys thereof. It is preferred to utilize the metals or metal alloy formed from a metal having a low molecular weight such as lithium or sodium since the mass change obtained as a result of absorbing water is larger and more easily detectable as compared to coatings containing higher molecular weight metals. The metal or metal alloy is deposited as a thin layer so that the sensing device is functional in a repeatable manner and that the hydroxide coating has adequate capacity to adsorb moisture less than about 5 microns thick, preferably between about 1 and about 0.01 microns thick.

The metal hydroxide composition coating derived from the metal composition coating has a lower moisture than a metal hydroxide coating formed from a metal hydroxide in solution which is applied to a support and then dehydrated at a temperature of 100° C. The method of metal hydroxide preparation of this invention thus provides substantial advantages over the method of impregnating porous solids with metal hydroxides. In the present invention it is unnecessary to heat the metal hydroxide to >100° C. to prepare the anhydrous form of the hydroxide. The hydrolysis reaction of the metal or metal alloy to form the hydroxide in this invention creates a porous structure within the film as it is hydrolyzed. Thus a porous support is unnecessary which is an advantage in the manufacture of the sensor. It also results in a desirable increase in the speed of response of the sensor and faster drydown recovery from the addition of moisture because of the absence of the support which also interacts with moisture and adds to the overall speed of response of the sensor. In addition, unlike thin metal coatings, the metal hydroxide composition coatings of this invention are not consumed by oxygen, carbon dioxide or moisture.

The detector of this invention is useful is monitoring water vapor impurity concentration in oxygen containing gases such as oxygen or nitrous oxide; inert gases, such as helium, argon, nitrogen, silicon containing gases such as silane; dopants such as arsine, phosphine, diborane; etchants such as halocarbon 14, halocarbon 16, halocarbon 218, sulfur hexafluoride, chlorine, or ammonia.

Referring to FIG. 1, the composite structure of this invention includes a piezoelectric crystal which is coated with the metal hydroxide coating composition of this invention set forth above to form coatings 12 and 14. Conductive lead wires 16 and 22 such as copper wire are bonded to crystal 10 electrodes 18 and 20 such as with solder or by mechanical means in order to input alternating electrical energy to crystal 10.

Figure 2:
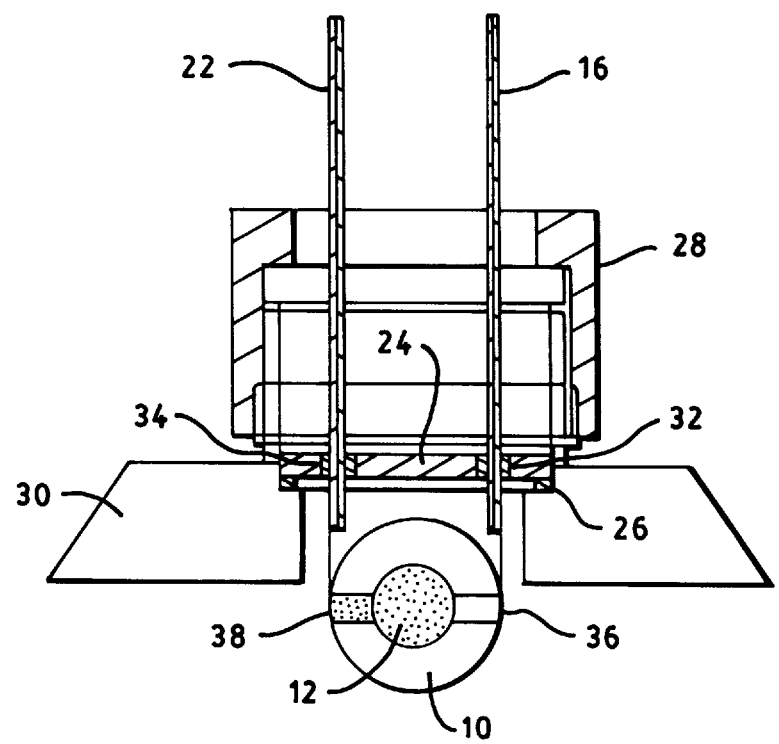
FIG. 2 is a side view of an apparatus of this invention using a piezoelectric crystal

Referring to FIG. 2, an apparatus of this invention is shown including the piezoelectric crystal mounted to lead wires by clips 36 and 38 via glass to metal seals 32 and 34 contained within housing platform 24. Housing platform 24 is sealed to base 30 by a metal face seal gasket 26 and nut 28. The lead wires 16 and 22 connect the crystal with coating 12 to form part of an electronic circuit which excites and monitors the frequency of oscillation of the energized crystal. The coatings 12 and 14 are applied by an acceptable thin film deposition technique, e.g., sputtering. The film is applied directly as the metal which then can be converted to the metal hydroxide by reaction with water. For the deposition of a metal conductor, e.g., barium or magnesium, DC sputtering is a possible mode. For other metals and alloys, e.g. barium, RF sputtering is also a suitable thin film deposition technique. In a process of utilizing the DC planar magnetron sputtering system for the deposition of barium, e.g., Model Arc-12 Planar Magnetron Sputtering System with a 300 watt DC power supply manufactured by Plasma Sciences, Inc. a potential is applied to a barium target. In the sputtering process, the barium target will become negatively self-biased creating an enrichment of ions in front of the target. The ions strike the target and sputtering is obtained. The crystal is positioned on a pedestal located at a distance of one to three inches from the bottom of the sputtering head. The crystal is masked so deposition occurs only on the desired areas of the piezoelectric electrodes. Typical sputtering operations with this piece of equipment are performed at a pressure range of 2 to 10 mtorr and DC power of 50 to 100 W with argon as the sputtering gas.

The piezoelectric crystal is a component in the feedback loop of an electronic circuit known as a Pierce Oscillator. The basic physics internal to the crystal is that of a standing sound wave set up within the crystal due to the application of an oscillating electric field to the crystal. In the Pierce circuit the crystal will oscillate at the frequency of the alternating electric field of the circuit applied to the crystal electrodes. When the frequency of the applied electric field is such that the wavelength of the standing wave produced is one-half the thickness of the crystal the crystal will oscillate at its maximum amplitude. This is the resonance oscillation frequency of the crystal. By changing the thickness, density, or mass of a coating applied to the surface of the crystal, a change in the resonance frequency of the crystal can be produced. This resonance frequency changes because the wavelength of the standing wave within the crystal changes as the thickness, mass, or density of the coating changes.

Two crystals and two separate Pierce oscillator circuits are used to measure frequency changes in the sensor crystal. One oscillator is used as a reference, the other as a mass sensor. The frequency output from the two oscillator circuits are fed into a logic circuit that gives the difference frequency of the two crystals. This serves two purposes; one to minimize temperature effects, the other to give a smaller frequency value, e.g., 5,000,000 Hz reference signal, and 4,999,000 Hz sensor signal, will produce a 1,000 Hz difference frequency.

Figure 3:
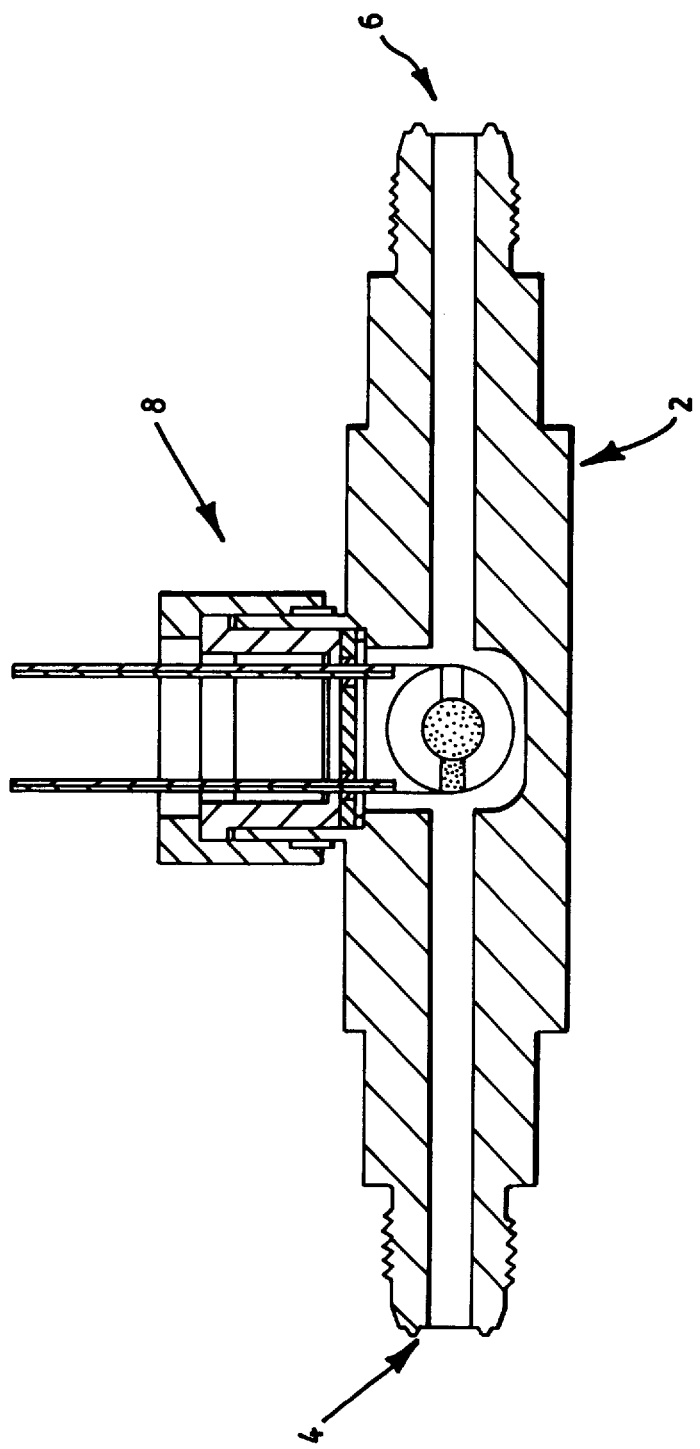
FIG. 3 is a schematic diagram illustrating the use of the apparatus of this invention.

Referring to FIG. 3, the sensor apparatus 8 of this invention is positioned on housing 2 and includes a gas inlet 4 and a gas outlet 6. Gas to be monitored is introduced through inlet 4. Monitored gas is passed through outlet 6 to a zone for chemical reaction (not shown). Alternate device configurations are possible, including a device in which the coated crystal is mounted directly within the flowing gas stream or in which a gas purifier, impurity generator and valves are positioned directly upstream of the sensor.

The following example illustrates the present invention and is not intended to limit the same.

EXAMPLE 1

A stainless steel housing consisting of all stainless steel components, metal-to-metal face seal and metal gasket seal connections and inlet and outlet diaphragm valves to seal the housing from outside atmosphere when required as constructed to permit testing of coated piezoelectric quartz crystals. An AT cut quartz crystal with fundamental frequency of 4.94 Mhz was DC sputter coated in an argon glove box with barium metal at 100 watts, 6 mTorr pressure for 15 minutes each side to deposit a total of 30 kHz of barium metal and decreased the frequency of the crystal to 4.91 Mhz. The crystal, was mounted between a pair of nickel clips in a stainless steel holder via glass feed-throughs. This crystal holder was inserted into the stainless steel housing and sealed with metal gasket seal. The housing was removed from the glove box and connected the oscillator electronic oscillator circuit through the leads connected to the nickel clips in the stainless steel platform. Connected to the sensor housing was a union tee with one leg connected to a source of nitrogen purified with a Waferpure Mini XL gas purifier and the second leg connected to a source of 1.3 part per million moisture in nitrogen. By mixing the purified and moist gas part per billion levels of moisture in nitrogen could be prepared. A flow of moisture was introduced to the barium coated sensor at a level of 1300 ppb for 24 hours at 20° C. After 24 hours the formed barium hydroxide coated sensor was purged with 0 part per billion moisture for 24 hours.

Figure 4:
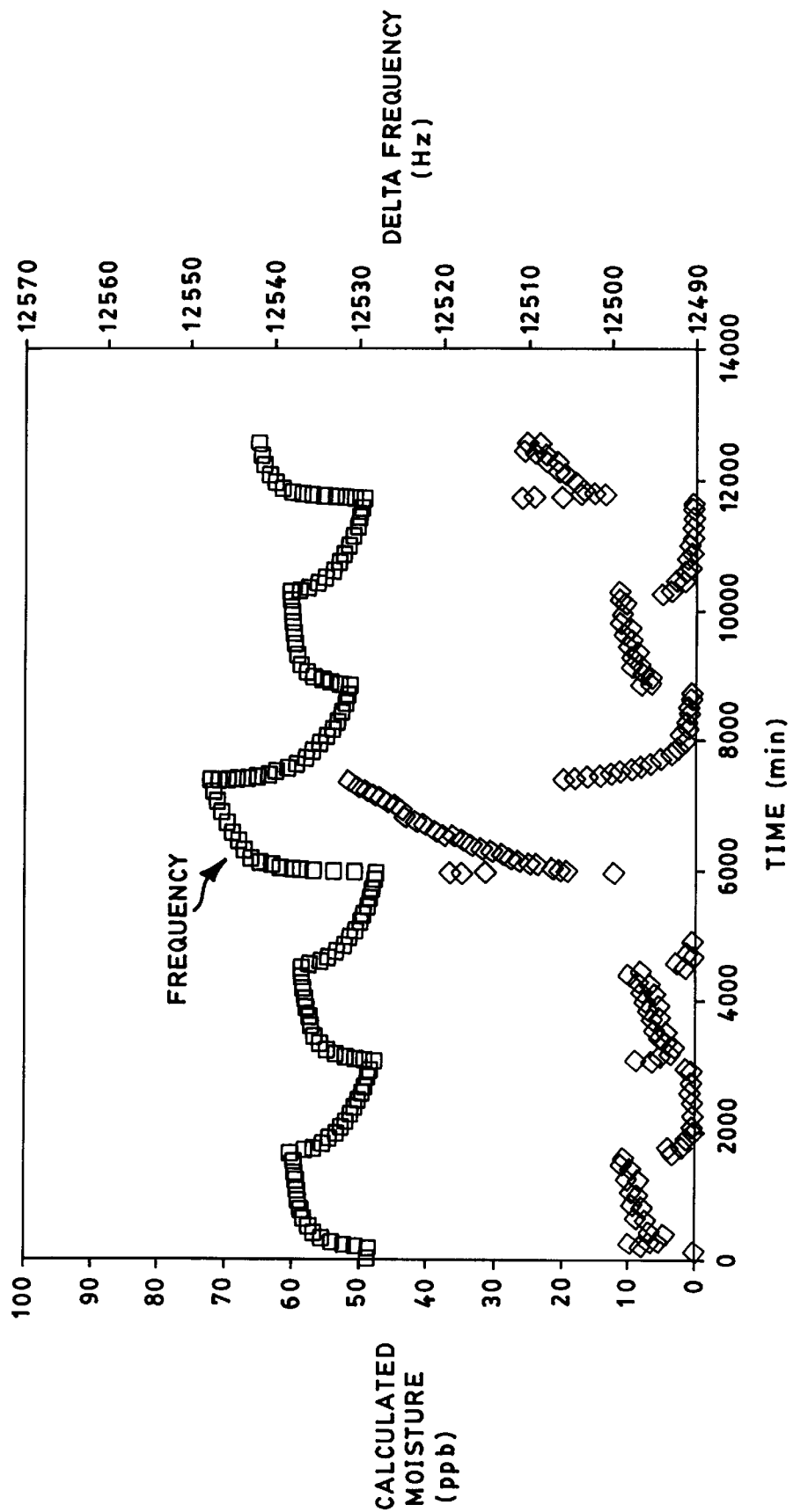
FIG. 4 is a graph showing gas moisture concentration and piezoelectric crystal frequency as a function of time.

By mixing 1.3 part per million moisture in nitrogen with volumes of dry nitrogen mixtures of part per billion moisture in nitrogen were prepared and delivered to the barium hydroxide coated sensor. As shown in FIG. 4, the sensing apparatus including the barium hydroxide coating is capable of measuring moisture concentrations in a gas to as low as about 10 ppb. FIG. 4 also shows the correlation between piezoelectric crystal vibration frequency and moisture content in the gas.

Figure 5:
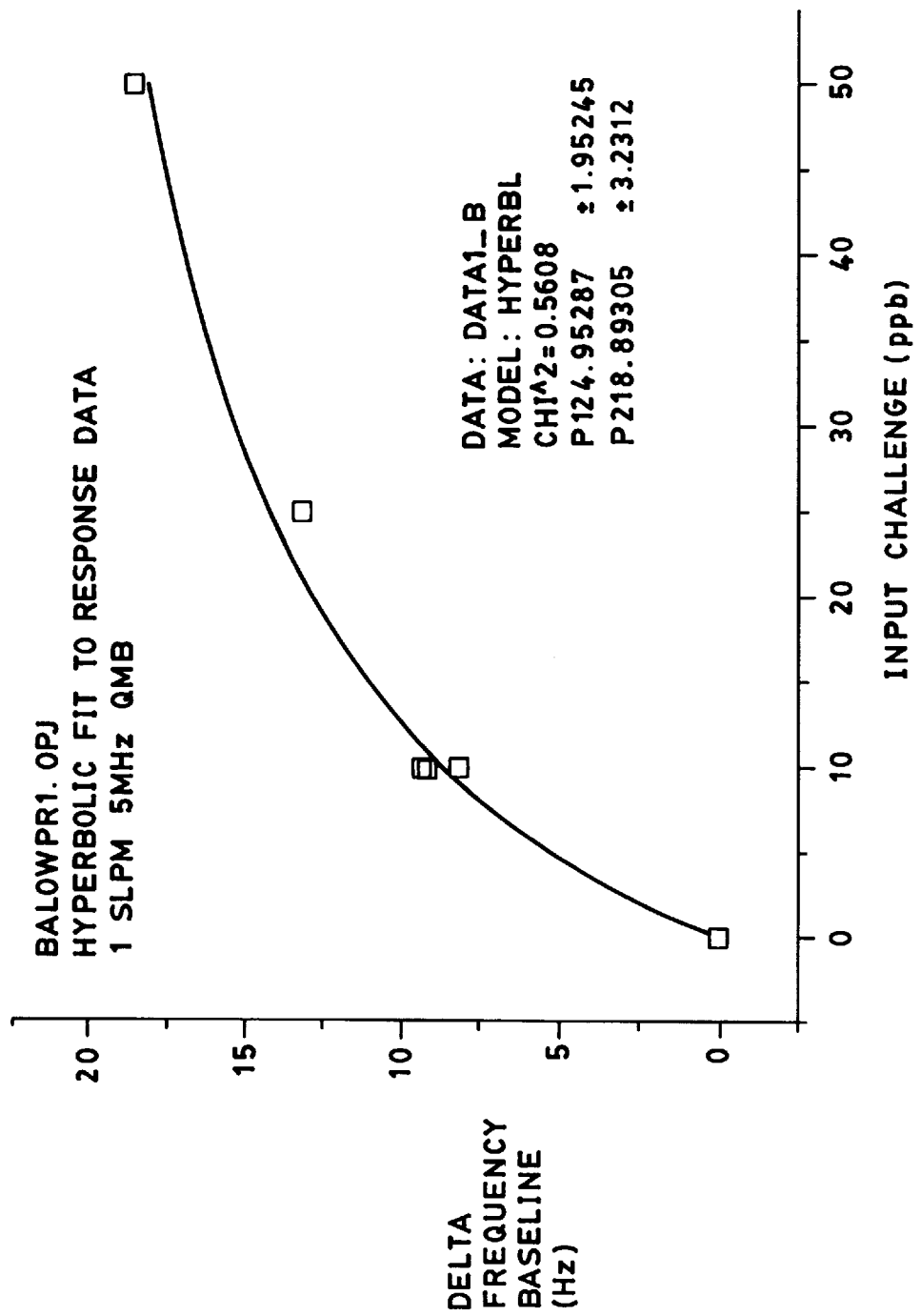
FIG. 5 is a calibration curve based upon FIG. 4.

FIG. 5 is the calibration curve for the barium hydroxide coated piezoelectric crystal sensing device based upon the data shown in FIG. 4. As shown in FIG. 5 the barium hydroxide is capable of measuring moisture to as low as about 1 part per billion.

EXAMPLE 2

A device consisted of all stainless steel and metal face sealed components to determine the ability of the barium hydroxide sensor to distinguish between purified and unpurified gas other than nitrogen. The sensor simulates the detection of moisture at the endpoint of a phosphine purifier.

All components were dried as described in Example 1. A 5 MHz quartz piezoelectric crystal coated with 30 KHz of barium metal and conditioned to barium hydroxide by exposure to 12 part per million moisture in phosphine gas. Purified phosphine gas was prepared using a Millipore Waferpure Mini XL (WPMV 200 SC) gas purifier.

Figure 6:
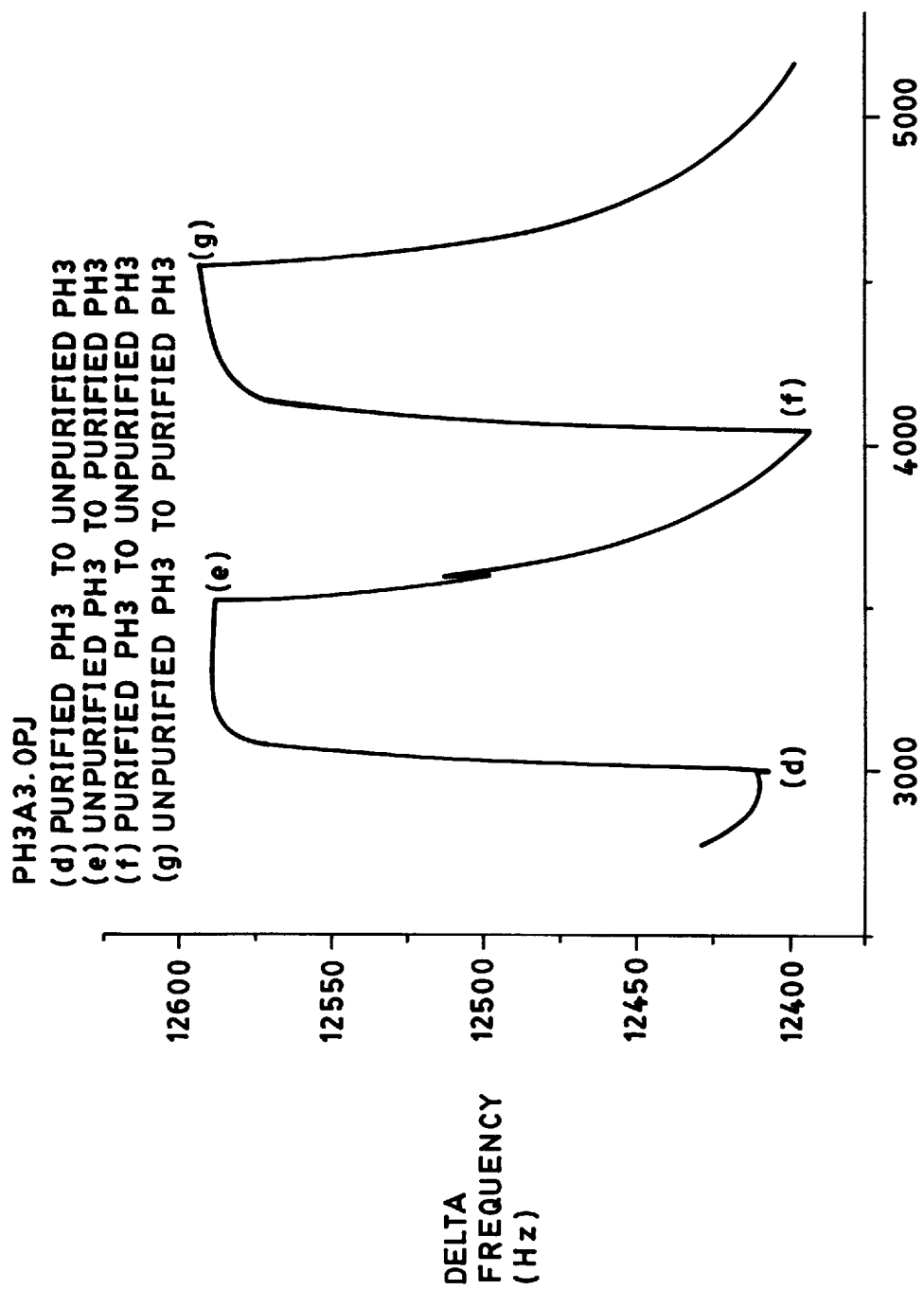
FIG. 6 is the response change of the sensor to purified and unpurified phosphine gas.

The barium hydroxide sensor was cycled between purified and unpurified phosphine gas at a flow rate of 70 sccm. During introduction of unpurified $PH_3$ gas to the sensor a frequency increase of the crystal due to adsorption of contaminant moisture was observed. When the phosphine gas was purified a decrease in the resonance frequency of the crystal was observed due to desorption of the contaminants from the barium hydroxide sensor coating. The response of the sensor crystal to purified and unpurified phosphine is shown in FIG. 6.

The invention claimed is:

1. A sensing device for measuring water content in a stream of gas which comprises:

a sensing device having an effective mass of a coating of a metal hydroxide composition of material formed in-situ derived from a metal composition by a conversion reaction of the metal composition with moisture in said gas stream, said coating having a mass which permits said material to produce a measurable physical response to energy input to said sensing device and means for applying energy to said sensing device and means for measuring said physical response.

2. The device of claim 1 wherein said sensing device has said coating on two opposing surfaces.

3. The device of claim 1 wherein said sensing device is a piezoelectric material.

4. The device of claim 2 wherein said sensing device is a piezoelectric material.

5. The device of claim 1 wherein said coating is barium hydroxide.

6. The device of claim 2 wherein said coating is barium hydroxide.

7. The device of claim 3 wherein said coating is barium hydroxide.

8. The device of claim 4 wherein said coating is barium hydroxide.

9. The device of claim 1 wherein said coating includes a layer of protective material between said metal hydroxide coating and said sensing device.

10. The device of claim 2 wherein said coating includes a layer of protective material between said metal hydroxide coating and said sensing device.

11. The device of claim 3 wherein said coating includes a layer of protective material between said metal hydroxide coating and said piezoelectric material.

12. The method for measuring water content in a gas stream which comprises contacting said gas stream with a sensing device having an effective mass of a metal hydroxide coating formed in-situ derived from a metal composition of material by a conversion reaction of the metal composition with moisture in said gas stream, said coating having a mass which permits said material to produce a measurable physical response to energy input to said sensing device, applying energy to said sensing device, and measuring said physical response and comparing said physical response to a standard relationship correlating said physical response to moisture content in said gas stream.

13. The method of claim 12 wherein said sensing device is a piezoelectric crystal.

14. The method of claim 12 wherein said sensing device is a capacitor having two plates and said metal hydroxide coating is positioned between said two plates.

15. The method of claim 12 wherein said coating is barium hydroxide.

16. The method of claim 12 wherein said coating includes a protective layer between said metal hydroxide coating and said sensing device.

17. The method of claim 13 wherein said coating is barium hydroxide.

18. The method of claim 13 wherein said coating includes a protective layer between said metal hydroxide coating and said sensing device.

* * * * *